(12) United States Patent
Pei et al.

(10) Patent No.: US 9,057,719 B2
(45) Date of Patent: Jun. 16, 2015

(54) FLUIDIC STRUCTURE WITH NANOPORE ARRAY

(71) Applicant: International Business Machines Corporation, Armonk, NY (US)

(72) Inventors: Chengwen Pei, Danbury, CT (US); Zhengwen Li, Danbury, CT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 13/771,929

(22) Filed: Feb. 20, 2013

(65) Prior Publication Data

US 2013/0164522 A1    Jun. 27, 2013

Related U.S. Application Data

(62) Division of application No. 12/843,228, filed on Jul. 26, 2010, now Pat. No. 8,535,544.

(51) Int. Cl.
*B32B 3/26* (2006.01)
*G01N 33/487* (2006.01)
*B81C 1/00* (2006.01)
*C30B 33/10* (2006.01)

(52) U.S. Cl.
CPC .......... *G01N 33/48721* (2013.01); *B32B 3/266* (2013.01); *B81B 2201/058* (2013.01); *B81B 2203/0384* (2013.01); *B81C 1/00087* (2013.01); *C30B 33/10* (2013.01)

(58) Field of Classification Search
CPC .............. C30B 33/10; B81B 2201/058; B81B 2203/0384; Y10T 428/24298; G01N 27/44791
USPC ..................... 428/304.4, 314.2; 422/502–504
See application file for complete search history.

(56) References Cited

U.S. PATENT DOCUMENTS

| 4,512,638 A | 4/1985 | Sriram et al. |
| 4,863,560 A | 9/1989 | Hawkins |
| 5,528,719 A | 6/1996 | Yamada |
| 5,569,620 A | 10/1996 | Linn et al. |

(Continued)

OTHER PUBLICATIONS

Kovacs, G.T.; Maluf, N.I.; Peterson, K.E. "Bulk Micromachining of Silicon" Proceedings of the IEEE, 1998, vol. 86, p. 1536-1551.*

(Continued)

*Primary Examiner* — Mark Ruthkosky
*Assistant Examiner* — Julia L Rummel
(74) *Attorney, Agent, or Firm* — Scully, Scott, Murphy & Presser, P.C.; H. Daniel Schnurmann

(57) ABSTRACT

A method of fabricating a material having nanoscale pores is provided. In one embodiment, the method of fabricating a material having nanoscale pores may include providing a single crystal semiconductor. The single crystal semiconductor layer is then patterned to provide an array of exposed portions of the single crystal semiconductor layer having a width that is equal to the minimum lithographic dimension. The array of exposed portion of the single crystal semiconductor layer is then etched using an etch chemistry having a selectivity for a first crystal plane to a second crystal plane of 100% or greater. The etch process forms single or an array of trapezoid shaped pores, each of the trapezoid shaped pores having a base that with a second width that is less than the minimum lithographic dimension.

16 Claims, 4 Drawing Sheets

(56) References Cited

U.S. PATENT DOCUMENTS

| | | | |
|---|---|---|---|
| 5,801,084 | A | 9/1998 | Beasom et al. |
| 6,515,845 | B1 | 2/2003 | Oh et al. |
| 6,627,067 | B1 | 9/2003 | Branton et al. |
| 6,638,885 | B1 | 10/2003 | McGrath et al. |
| 6,960,298 | B2 | 11/2005 | Krotz et al. |
| 6,998,324 | B2 | 2/2006 | Seo |
| 7,045,851 | B2 | 5/2006 | Black et al. |
| 7,217,562 | B2 | 5/2007 | Cao et al. |
| 7,223,894 | B2 | 5/2007 | Chau et al. |
| 7,248,771 | B2 | 7/2007 | Schmidt et al. |
| 7,250,544 | B2 | 7/2007 | Chau et al. |
| 7,267,781 | B2 | 9/2007 | Steinberg et al. |
| 7,274,078 | B2 | 9/2007 | Jaiprakash et al. |
| 7,444,053 | B2 | 10/2008 | Schmidt et al. |
| 7,489,616 | B2 | 2/2009 | Takahashi et al. |
| 7,531,407 | B2 | 5/2009 | Clevenger et al. |
| 7,560,224 | B2 | 7/2009 | Sato et al. |
| 7,582,490 | B2 | 9/2009 | Golovchenko et al. |
| 7,586,618 | B2 | 9/2009 | Marks et al. |
| 7,588,993 | B2 | 9/2009 | Liu et al. |
| 7,610,074 | B2 | 10/2009 | Boppart et al. |
| 7,626,246 | B2 | 12/2009 | Lochtefeld et al. |
| 7,709,341 | B2 | 5/2010 | Fucsko et al. |
| 8,114,306 | B2 | 2/2012 | Cheng et al. |
| 2002/0086455 | A1 | 7/2002 | Franosch et al. |
| 2008/0025875 | A1* | 1/2008 | Martin et al. ............. 422/82.01 |
| 2008/0277006 | A1 | 11/2008 | Moon et al. |
| 2009/0115094 | A1 | 5/2009 | Chou et al. |
| 2009/0142825 | A1* | 6/2009 | Murray et al. ............. 435/287.1 |
| 2009/0184423 | A1 | 7/2009 | Erturk et al. |
| 2010/0029550 | A1 | 2/2010 | Austin et al. |
| 2010/0051944 | A1 | 3/2010 | Kato et al. |
| 2010/0230674 | A1 | 9/2010 | Barbe et al. |

OTHER PUBLICATIONS

Ileri, N.; Letant, S.E.; Britten, J.; Nguyen, H.; Larson, C.; Zaidi, S.; Palazoglu, A.; Faller, R.; Tringe, J.W.; Stroeve, P.; "Efficient Nanoporous Silicon Membranes for Integrated Microfluidic Separation and Sensing Systems" Materials Research Society Symposium Proceedings, Jan. 2009, 1191-OO09-02, p. 1-6.*

Storm, A.J.; Chen, J.H.; Lin, X.S.; Zanderbergen, H.W.; Dekker, C.; "Electron-beam-induced deformations of SiO2 nanostructures" Journal of Applied Physics, 2005, 98, p. 014307-1-014307-7.*

Office Action received in a related U.S. Appl. No. 12/843,228.

* cited by examiner

FLUIDIC STRUCTURE WITH NANOPORE ARRAY

CROSS REFERENCE TO RELATED APPLICATION

This application is a divisional of U.S. patent application Ser. No. 12/843,228, filed Jul. 26, 2010 the entire content and disclosure of which is incorporated herein by reference.

BACKGROUND

The present disclosure relates to methods of forming structures including porosity, such as fluidic channels.

The use of pore containing materials, such as fluidic channels, is known for the treatment and observation of, research on, or even the culturing of living cells. For example, fluidic channels including pores are in some instances suitable for DNA sequencing, and molecular sensors. Pore containing materials are also suitable for water filtration. Porosified semiconductor materials are one type of material that may be utilized in the above applications.

SUMMARY

A method of fabricating a material having nanoscale pores is provided. In one embodiment, crystallographic etching methods in combination with the thickness and the composition of the material containing the nanoscale pores is selected to control the diameter, i.e., width, of the nanoscale pores. In one embodiment, the method of fabricating a material having nanoscale pores may include providing a single crystal semiconductor layer. The single crystal semiconductor layer can be patterned to provide an array of exposed portions of the single crystal semiconductor layer having a first width that is equal to the minimum lithographic dimension. The array of exposed portions of the single crystal semiconductor layer can be etched using an etch chemistry having a selectivity for etching a first crystal plane selective to a second crystal plane. The etch process forms an array of trapezoid shaped pores, each of the trapezoid shaped pores having a base with a second width that is less than the minimum lithographic dimension.

In another embodiment, the method of fabricating a material having nanoscale pores may include providing a semiconductor on insulator (SOI) substrate, wherein the semiconductor on insulator substrate includes a single crystal semiconductor layer on a dielectric layer. The dielectric layer is present on a base semiconductor layer. The single crystal semiconductor layer is patterned to provide an array of exposed portions of the single crystal semiconductor layer having a first width that is equal to the minimum lithographic dimension. The array of exposed portions of the single crystal semiconductor layer is then etched using an etch chemistry that etches a first crystal plane of the single crystal semiconductor layer selective to a second crystal plane of the single crystal semiconductor layer. The etch process that forms the array of trapezoid shaped pores terminates on the dielectric layer. Each of the trapezoid shaped pores have a base with a second width that is less than the minimum lithographic dimension. The etch process may terminate on the dielectric layer. The dielectric layer may then be etched to provide a fluidic channel between at least two pores of the array of trapezoid shaped pores.

In another aspect, a structure is provided including an array of nanopores formed in a single crystal semiconductor material. Each nanopore of the array of nanopores has a trapezoid shaped geometry. The diameter at a first end of each of the nanopores in the array of nanopores is greater than the minimum lithographic dimension. The diameter at a second end of each of the nanopores in the array of nanopores is less than the minimum lithographic dimension.

DESCRIPTION OF THE DRAWINGS

The following detailed description, given by way of example and not intended to limit the invention solely thereto, will best be appreciated in conjunction with the accompanying drawings, wherein like reference numerals denote like elements and parts, in which.

DETAILED DESCRIPTION

Figure 1:
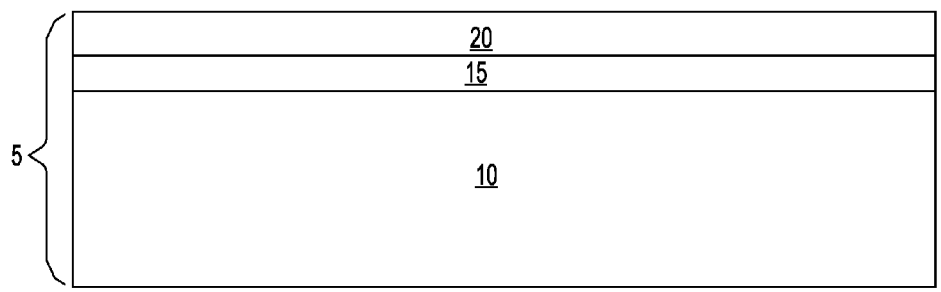
FIG. 1 is a side cross-sectional view depicting one embodiment of a semiconductor substrate, i.e., semiconductor on insulator (SOI) substrate, including at least a single crystal semiconductor layer overlying a dielectric layer, as used in accordance with the present disclosure.

Detailed embodiments of the present disclosure are disclosed herein; however, it is to be understood that the disclosed embodiments are merely illustrative of the present disclosure that may be embodied in various forms. In addition, each of the examples given in connection with the various embodiments of the present invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. For purposes of the description hereinafter, the terms "upper", "lower", "right", "left", "vertical", "horizontal", "top", "bottom", and derivatives thereof shall relate to the invention, as it is oriented in the drawing figures. The terms "overlying", "atop", "positioned on" or "positioned atop" means that a first element, such as a first structure, is present on a second element, such as a second structure, wherein intervening elements, such as an interface structure, e.g. interface layer, may be present between the first element and the second element. The term "direct contact" means that a first element, such as a first structure, and a second element, such as a second structure, are connected without any intermediary conducting, insulating or semiconductor layers at the interface of the two elements.

In one embodiment, a method of forming a nanopore array is provided, in each pore of the nanopore array has a trapezoid shaped cross section. The term "nanopore" denotes an opening having a maximum dimension, e.g., radius, that is equal to 100 nm or less. The term "trapezoid-shaped" means a four-sided figure with one pair of parallel sides. In one embodiment, the trapezoid shaped nanopore has the geometry of an isosceles trapezoid, in which the non-parallel sides and base angles of the trapezoid are equal.

In one embodiment, the width of the trapezoid shaped nanopore is less than the minimum lithographic dimension. The "minimum lithographic dimension" means the smallest dimension obtainable by lithography. In some examples, the minimum lithographic dimension that a projection system can print is given approximately by:

$$CD = k_1 \cdot (\lambda/NA)$$

CD is the minimum lithographic dimension
$k_1$ is a coefficient that encapsulates process-related factors (typically equals 0.4)
$\lambda$ is the wavelength of light
NA is the numerical aperture of the lens of the photolithography device.

In one embodiment, the longer side, i.e., first width, of the parallel sides of the trapezoid shaped nanopore has a dimension that is equal to or greater than the minimum lithographic dimension, and the shorter side, i.e., second width, of the parallel sides of the trapezoid shaped nanopore that is less than the minimum lithographic dimension. Typically, the minimum lithographic dimension ranges from 15 nm to 20 nm. In one embodiment, pore openings of nanoscale dimension are provided by a method that employs single crystal semiconductor materials in combination with crystalline etching, as depicted in FIGS. 1-3.

Figure 2:
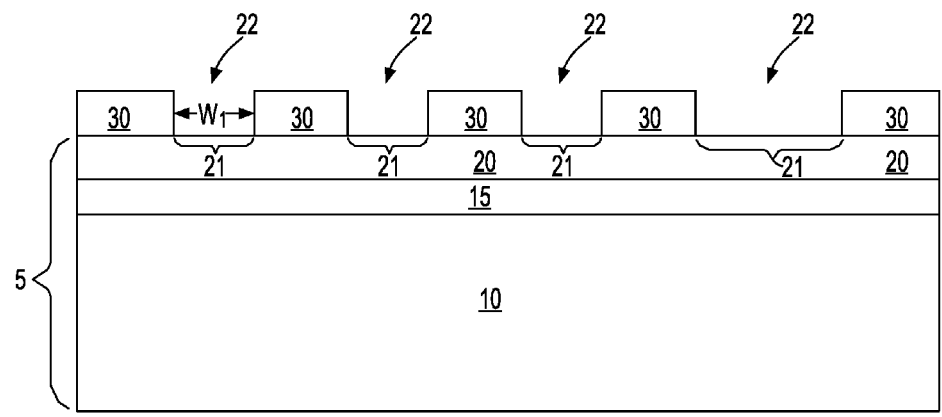
FIG. 2 is a side cross-sectional view depicting patterning the single crystal semiconductor layer to provide an array of exposed portions of the single crystal semiconductor layer, in which each of the exposed portions of the single crystal semiconductor layer has a first width that is equal to or greater than a minimum lithographic dimension, in accordance with one embodiment of the present disclosure.

FIG. 1 illustrates one embodiment of a substrate 5, i.e., semiconductor on insulator (SOI) substrate, which is suitable for forming a trapezoid shaped nanopore array. The substrate 5 may include at least a single crystal semiconductor layer 20 overlying a dielectric layer 15. A base semiconductor substrate 10 may be present underlying the dielectric layer 15.

The single crystal semiconductor layer 20 may comprise any single crystal semiconducting material including, but not limited to, Si, strained Si, SiC, SiGe, SiGeC, Si alloys, Ge, Ge alloys, GaAs, InAs, AlAs and InP, or any combination thereof. A single crystal semiconductor material is a crystalline solid in which atoms are arranged following a specific pattern throughout the entire piece of the material, i.e., a long-range order exists throughout. In contrast, a polycrystalline material is a material in which a long-range order exists only within a portion of the grains, wherein the grains are randomly connected to form a solid. In a polycrystalline material there is no preferential extension of the single-crystal within the grain in any direction. In contrast to polycrystalline and single crystal materials, an amorphous material is a non-crystalline solid with no periodicity and no long-range order at all.

The single crystal semiconductor layer 20 may be thinned to a desired thickness by planarization, grinding, wet etch, dry etch, or any combination thereof. One method of thinning the single crystal semiconductor layer 20 is to oxidize the Si by a thermal dry or wet oxidation process, and then wet etch the oxide layer using a hydrofluoric acid mixture. This process can be repeated to achieve the desired thickness. In one embodiment, the single crystal semiconductor layer 20 has a thickness ranging from 10.0 nm to 100.0 nm. In another embodiment, the single crystal semiconductor layer 20 has a thickness ranging from 20.0 nm to 90.0 nm. In yet another embodiment, the single crystal semiconductor layer 20 has a thickness ranging from 30.0 nm to 80.0 nm. In one embodiment, the single crystal semiconductor layer 20 is doped with a p-type dopant or an n-type dopant. As used herein, "n-type" refers to the addition of impurities that contributes free electrons to an intrinsic semiconductor. In a silicon containing substrate examples of n-type dopants, i.e., impurities, include but are not limited to antimony, arsenic and phosphorous. In one embodiment, a single crystal semiconductor layer 20 that is doped with an n-type dopant, the n-type dopant is present in a concentration ranging from $1 \times 10^{15}$ atoms/cm$^3$ to $1 \times 10^{22}$ atoms/cm$^3$. In another embodiment, the single crystal semiconductor layer that is doped with an n-type dopant has an n-type dopant concentration ranging from $1 \times 10^{17}$ atoms/cm$^3$ to $1 \times 10^{20}$ atoms/cm$^3$. As used herein, a "p-type" refers to the addition of trivalent impurities to an intrinsic semiconductor that creates deficiencies of valence electrons. In one example, the addition of boron, aluminum, or gallium to a type IV semiconductor, such as Si, creates deficiencies of valence electrons. In one embodiment, a single crystal semiconductor layer 20 that is doped with a p-type dopant, the p-type dopant is present in a concentration ranging from $5 \times 10^{15}$ atoms/cm$^3$ to $5 \times 10^{21}$ atoms/cm$^3$. In another embodiment, the single crystal semiconductor layer 20 is doped with a p-type dopant that is present in a concentration ranging from $1 \times 10^{16}$ atoms/cm$^3$ to $1 \times 10^{20}$ atoms/cm$^3$.

The dielectric layer 15 that can be present underlying the single crystal semiconductor layer 20 and atop the base semiconductor substrate 10 may be formed by implanting a high-energy dopant into the substrate 5 and then annealing the structure to form a buried oxide layer, i.e., dielectric layer 15. In another embodiment, the dielectric layer 15 may be deposited or grown prior to the formation of the single crystal semiconductor layer 20. In yet another embodiment, the substrate 5 may be formed using wafer-bonding techniques, where a bonded wafer pair is formed utilizing glue, adhesive polymer, or direct bonding.

FIG. 2 depicts one embodiment of patterning the single crystal semiconductor layer 20 to provide an array of exposed portions 21 of the single crystal semiconductor layer 20. Each of the exposed portions 21 of the single crystal semiconductor layer 20 has a first width W1 that is equal to or greater than a minimum lithographic dimension. The minimum lithographic dimension may vary with the photolithography apparatuses being used to form the etch mask 30, but typically ranges from 15 nm to 20 nm. In one embodiment, the width, i.e., first width W1, of each of the exposed portions 21 of the single crystal semiconductor layer 20 is greater than 20 nm. For example, the width, i.e., first width W1, of each of the exposed portions 21 of the single crystal semiconductor layer 20 may range from 20 nm to 100 nm. In another example, the width, i.e., first width W1, of each of the exposed portions 21 of the single crystal semiconductor layer 20 may range from 25 nm to 80 nm.

In one embodiment, the patterning of the single crystal semiconductor layer 20 to provide an array of exposed portions 21 of the single crystal semiconductor layer 20 includes depositing a photoresist layer on the single crystal semiconductor layer 20, and exposing the photoresist layer to radiation to provide a pattern corresponding to the underlying portions of the single crystal semiconductor layer 20 that becomes the exposed portions 21 of the single crystal semiconductor layer 20. Following application of the radiation, the irradiated portions of the photoresist layer are developed utilizing a resist developer to provide a first etch mask 30 having openings 22 defining the exposed portions 21 of the single crystal semiconductor layer 20.

In one embodiment, a hardmask (not shown) may be used to define the exposed portions 21 of the single crystal semiconductor layer 20. The hardmask may be formed by depositing a dielectric hardmask material, like SiN or $SiO_2$, atop the single crystal semiconductor layer 20 and then applying a photoresist pattern to the dielectric hardmask material using a lithography process steps. The photoresist pattern is then transferred into the hardmask material using a dry etch process forming the hardmask.

FIG. 3 depicts one embodiment of etching the array of exposed portions 21 of the single crystal semiconductor layer 20. The etch chemistry for etching the array of exposed portions 21 of the single crystal semiconductor layer 20 may have a selectivity for a first crystal plane of the single crystal semiconductor layer 20 to a second crystal plane of single crystal semiconductor layer 20. In one embodiment, the etch process forms an array of trapezoid shaped pores 35. The term "array" denotes a plurality of trapezoid shaped pores 35. In one embodiment, the array of trapezoid shaped pores 35 includes a concentration of trapezoid shaped pores 35 that ranges from 100 $^3$pores/$cm^2$ to $10^{10}$ pores/$cm^2$. In another embodiment, the array of trapezoid shaped pores 35 includes a concentration of trapezoid shaped pores 35 that ranges from 10000 pores/$cm^2$ to $10^6$ pores/$cm^2$. In yet another embodiment, the array of trapezoid shaped pores 35 includes a concentration of trapezoid shaped pores 35 that ranges from 10 pores/$cm^2$ to 100 pores/$cm^2$. In another embodiment, a single trapezoid shaped nanopore 35 may be provided for DNA sequencing.

The array of exposed portions 21 of the single crystal semiconductor layer 20 may be etched using a selective crystallographic etching method. A crystallographic etching method uses an etch chemistry having a selectivity for a first crystal plane of the single crystal semiconductor layer 20 to a second crystal plane of the single crystal semiconductor layer 20. As used herein, the terms "selective" and "selectivity" in reference to a material removal process denotes that the rate of material removal for a first material is greater than the rate of removal for at least another material of the structure to which the material removal process is being applied. For example, in one embodiment, the selectivity for removing the first crystal plane to the second crystal plane is greater than 100%. In another embodiment, the selectivity for removing the first crystal plane to the second crystal plane is greater than 200% and less than 600%. In yet another embodiment, the selectivity for removing the first crystal plane to the second crystal plane is greater than 400. The crystallographic etch may also be selective to the material of the dielectric layer 15. In this embodiment, the crystallographic etch terminates on the dielectric layer 15.

In one embodiment, in which the single crystal semiconductor layer 20 is a silicon-containing material, the first crystal plane is <100> and the second crystal plane is <111>, in which the first crystal plane is etched selectively to the second crystal plane. The <100> crystal plane of the single crystal semiconductor layer 20 extends along a direction that is parallel to the upper surface of the single crystal semiconductor layer 20.

In one embodiment, in which the single crystal semiconductor layer 20 is a silicon-containing material, such as silicon, the selectivity of the crystallographic etch provides an isosceles trapezoid shaped pore 35, in which the angle, i.e., acute angle, at the intersection of the sidewall S1 of the isosceles trapezoid shaped pore 35 and the upper surface of the dielectric layer 15 is approximately 54 degrees. In one embodiment, in which the second crystal plane is <111>, and the etchant etches the <100> crystal plane of the single crystal semiconductor layer 20 selective to the <111> crystal plane, the sidewall Si of the isosceles trapezoid shaped pore 35 extends along the <111> direction. It is noted that other materials may be provided for the single crystal semiconductor layer 20, and that the present disclosure should not be limited to the above example, in which the single crystal semiconductor layer 20 is composed of silicon. Other materials that can be crystallographically etched to provide a trapezoid shaped pore 35 are within the scope of the methods and structures disclosed herein. For example, in some embodiments, the single crystal semiconductor layer 20 that is crystallographically etched to provide the trapezoid shaped pore 35 may include, but is not limited to Si, Ge, SiGe, GaAs, InAs, AlAs or combinations and multi-layers thereof.

Figure 3A:
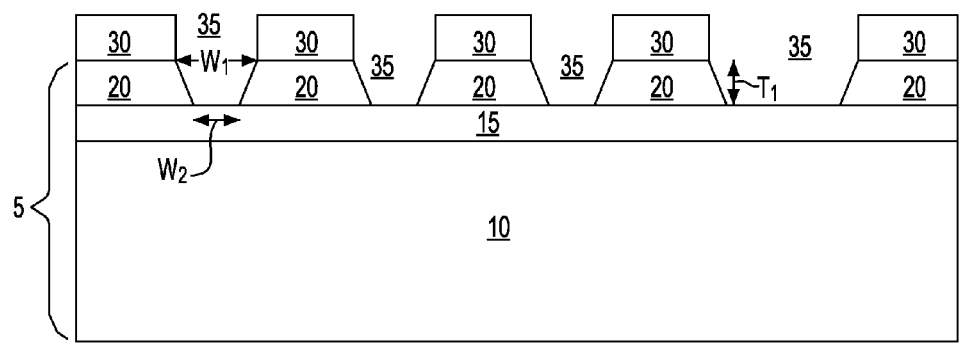
FIG. 3A is a side cross-sectional view depicting etching the array of exposed portions of the single crystal semiconductor layer using an etch chemistry having a selectivity for a first crystal plane of the single crystal semiconductor layer to a second crystal plane of single crystal semiconductor layer, wherein the etch process forms an array of trapezoid shaped pores, each of the trapezoid shaped pores having a base with a second width that is less than the minimum lithographic dimension, in accordance with one embodiment of the present disclosure.

Referring to FIG. 3A, and in one embodiment, the diameter, i.e., first width W1, of a first opening at a first end, i.e., upper surface, of the trapezoid shaped nanopore 35 is greater than the minimum lithographic dimension, and the diameter, i.e., second width W2, of a second opening at a second end of the trapezoid shaped nanopores 35 is less than the minimum lithographic dimension. The first and second openings are positioned on opposing sides of the trapezoid shaped nanopore 35 and are in fluid communication. In one example, the opening at the first end of the trapezoid shaped nanopore has a width, i.e., diameter, that is equal to the width W2 defined by the openings in the etch mask 30. In some instances, because the openings in the etch mask 30 are defined by photolithography, the minimum width, i.e., diameter, of the first opening may be equal to the minimum lithographic dimension or may be greater than the minimum lithographic dimension.

Figure 3B:
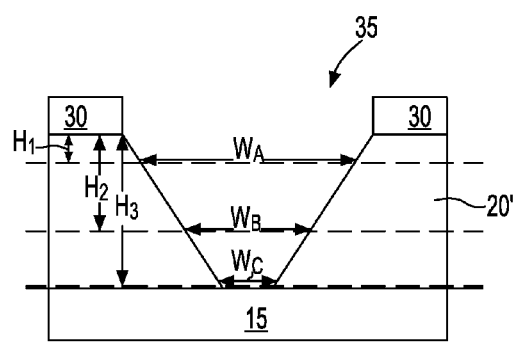
FIG. 3B is a side cross sectional view of one embodiment of a trapezoid shaped nanopore, in which the width of the base of the trapezoid shaped nanopore is related to the height of the trapezoid shaped nanopore.

In some embodiments, the crystallographic etch that is applied to the exposed portions 21 of the single crystal semiconductor layer 30 results in a tapered pore (trapezoid shaped pore 35), wherein the width of the trapezoid shaped pore 35 reduces with in increasing depth into the single crystal semiconductor layer 20 from the first opening of the trapezoid shaped pore 35. Therefore, because the width of the trapezoid shaped pore 35 reduces with increasing depth into the single crystal semiconductor layer 20, the diameter, i.e., second width, of the second opening at the base of the trapezoid shaped pore 35 is less than the minimum lithographic dimension. FIG. 3B illustrates that as the thickness of the single crystal semiconductor layer 20 increases and the height of the trapezoid shaped nanopore increases, e.g., H1<H2<H3, the width of second opening at the base of the trapezoid shaped pore 35 decreases, e.g., Wa>Wb>Wc.

Referring to FIGS. 3A, one example of an etchant suitable for crystallographic etching of the single crystal semiconductor layer 20 is potassium hydroxide (KOH). Potassium hydroxide (KOH) etches the <100> plane of silicon selective to the <111> plane of silicon. In one embodiment, potassium hydroxide (KOH) may provide an etch selectivity of 400 between the <100> and <111> crystal planes. Other examples of etchants that may provide isosceles trapezoid shaped pore 35 include ethylene diamine and pyrocatechol (EDP).

Referring to FIG. 3A, the base of the trapezoid shaped pore 35 has a width, i.e., second width W2, that is less than the first width W1 at the upper surface of the trapezoid shaped pore 35, and is therefore less than the minimum lithographic dimension. In one embodiment, the width of the base, i.e., second width W2, of the trapezoid shaped pore 35 may be dictated by selecting the thickness T1 of the single crystal semiconductor layer 20 in combination with the material of the single crystal semiconductor 20 in combination with the crystalline etching method. In the embodiments, in which the angle α, i.e., acute angle, at the intersection of the sidewall S1 of the isosceles trapezoid shaped pore 35 and the upper surface of the dielectric layer 15 is approximately 54 degrees, the width of the base, i.e., second width W2, of the trapezoid shaped pore 35 may be dictated by the equation:

$$W1 = W2 + (2 \times T1 \times COS/SIN\ 54°)$$

W1 is the first width at the upper surface of the trapezoid shaped pore

W2 is the second width at the base of the trapezoid shaped pore

T1 is the thickness of the single crystal semiconductor layer 20.

Referring to FIG. 3A, and in one embodiment, each of the trapezoid shaped pores 35 of the array of trapezoid shaped pores 35 has a base with a second width W2 that is less than the minimum lithographic dimension. In one example, the base of each of the trapezoid shaped pores 35 has a width, i.e., second width W2, ranging from 1 nm to 15 nm. In another example, the base of each of the trapezoid shaped pores 35 ranges from 2 nm to 10 nm. In yet another example, the base of each of the trapezoid shaped pores 35 ranges from 5 nm to 7 nm. The width, i.e., first width W1, at the first end, i.e., upper surface, of the first opening each of the trapezoid shaped pores 35 is greater than 20 nm. For example, the width, i.e., first width W1, of each of the first opening to each of the trapezoid shaped pores 35 may range from 21 nm to 100 nm. In another example, the width, i.e., first width W1, of the first opening to each of the trapezoid shaped pores 35 may range from 25 nm to 80 nm.

In one embodiment, the crystallographic etching provides uniformity for the second width W2 at the second opening of the trapezoid shaped pores 35 not previously capable of being produced by prior methods. In one embodiment, the standard deviation of the second width W2 of the opening at the second end of each trapezoid shaped nanopore 35 of the array of trapezoid shaped nanopores 35 ranges from 1 to 10 nm. In another embodiment, the standard deviation of the second width W2 of the second end of each trapezoid shaped nanopore 35 of the array of nanopores 35 ranges from 1 to 5 nm. In yet another embodiment, the standard deviation of the second width W2 of the second end of each trapezoid shaped nanopore 35 of the array of nanopores 35 ranges from 1 to 3 nm.

Figure 4:
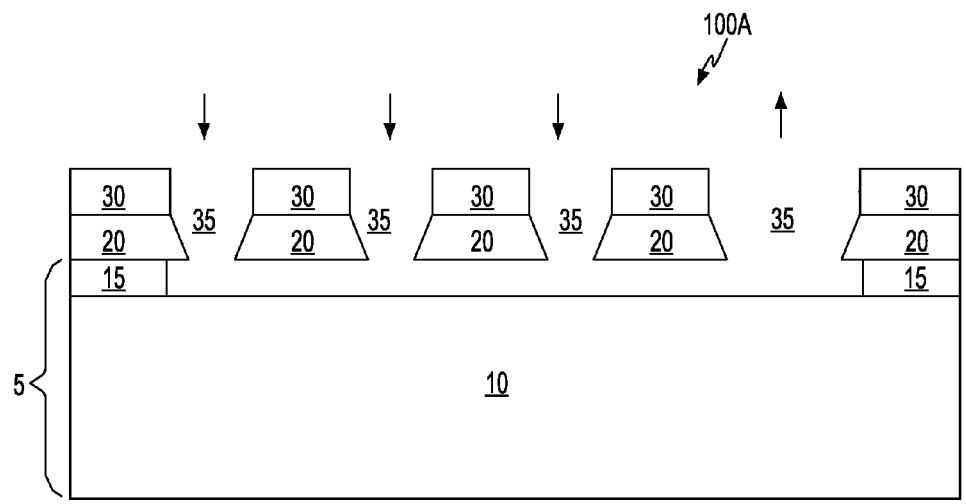
FIG. 4 is a side cross-sectional view depicting etching the dielectric layer to provide a fluidic channel between at least two trapezoid shaped pores of the array of trapezoid shaped pores, in accordance with one embodiment of the present disclosure.

FIG. 4 depicts etching the dielectric layer 15 to provide a fluidic channel 100A between at least two trapezoid shaped pores 35 of the array of trapezoid shaped pores 35. In one embodiment, at least a portion of the dielectric layer 15 is removed using an isotropic etch. An isotropic etch process is a material removal process in which the rate of the etching reaction is substantially similar in any direction. The etch process may include a plasma etch or a wet etch. The etchant is introduced to the dielectric layer 15 through the trapezoid shaped pores 35. When the buried dielectric layer 15 comprises a silicon oxide dielectric material, the isotropic etchant may include a dilute hydrofluoric acid etchant or a dilute buffered hydrofluoric acid etchant. The present disclosure is not, however, limited to the foregoing materials compositions. The remaining portion of the dielectric layer 15 provides pedestals that support the remaining portions of the single crystal semiconductor layer 20.

Figure 5:
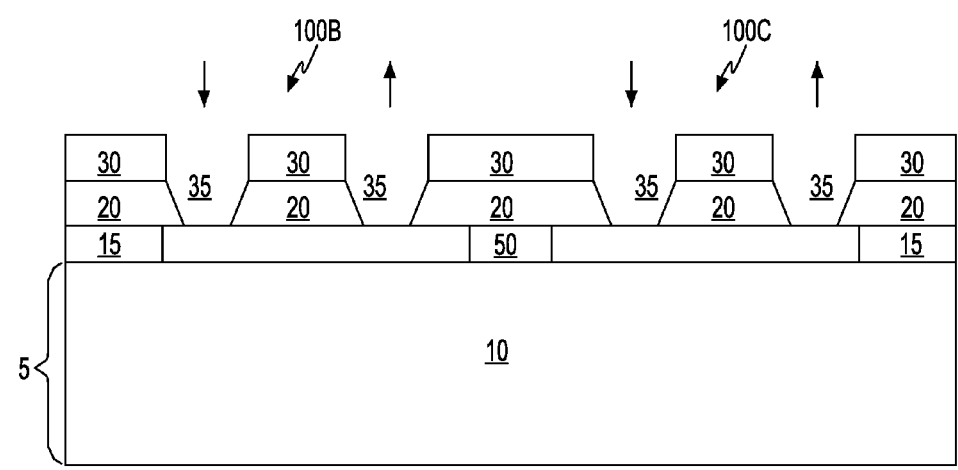
FIG. 5 is a side cross-sectional view depicting etching the dielectric layer to provide two fluidic channels, wherein each fluidic channel is between at least two trapezoid shaped pores of the array of trapezoid shaped pores, in accordance with another embodiment of the present disclosure.

In the embodiment depicted in FIG. 4, the fluidic channel 100A includes three trapezoid shaped pores 35 as an inlet to the fluidic channel 100A and a single trapezoid shaped pore 35 as the exit of the fluidic channel 100A, in which the arrows depict the flow of fluid through the fluidic channel 100A. FIG. 5 depicts another embodiment of a fluidic channel 100B, 100C that may be formed using the above-described method. More specifically, the embodiment depicted in FIG. 5 includes two fluidic channels 100B, 100C separated by a pedestal region 50. Each fluidic channel 100B, 100C includes a single inlet provided by a trapezoid shaped pore 35 and a single outlet provided by a trapezoid shaped pore 35, in which the arrows depict the flow of fluid through the fluidic channels 100B, 100C.

Figure 6:
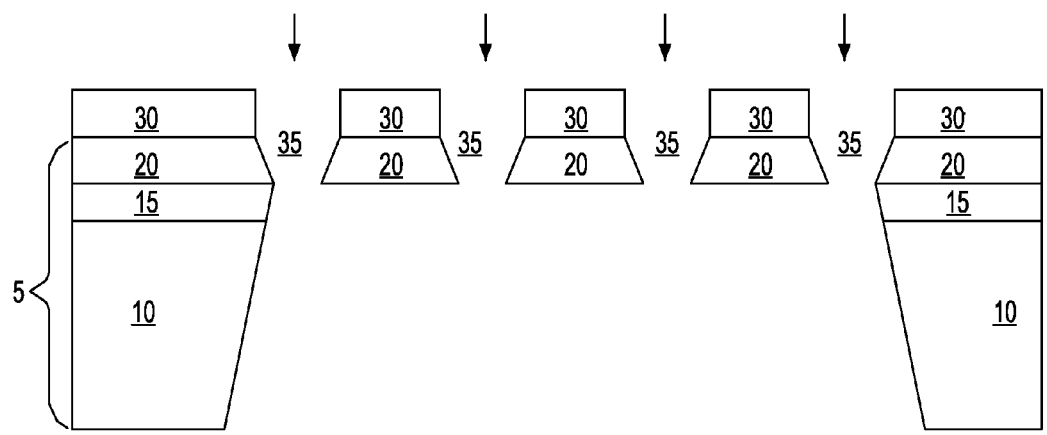
FIG. 6 is a side cross-sectional view depicting etching the dielectric layer and the base semiconductor substrate to provide a fluidic channel, in accordance with another embodiment of the present disclosure.

FIG. 6 depicts another embodiment of a fluidic channel 100D. In this embodiment, the dielectric layer 15 is removed using an isotropic etch, as depicted in FIG. 4. Following removal of the dielectric layer 15, a portion of the base semiconductor substrate 10 may be removed to provide a fluidic channel 100D that extends through the entire semiconductor substrate 5. In one embodiment, the base semiconductor substrate 10 may be removed by an anisotropic etch, such as a reactive ion etch. An anisotropic etch process is a material removal process in which the etch rate in the direction normal to the surface to be etched is much higher than in the direction parallel to the surface to be etched. Reactive ion etch is a form of plasma etching, in which the surface to be etched is placed on the RF powered electrode and takes on a potential that accelerates an etching species, which is extracted from a plasma, towards the surface to be etched, wherein a chemical etching reaction takes place in the direction normal to the surface being etched. In one embodiment, a second etch mask may be provided in direct contact with the base semiconductor substrate 10 by a patterned photoresist layer.

Figure 7:
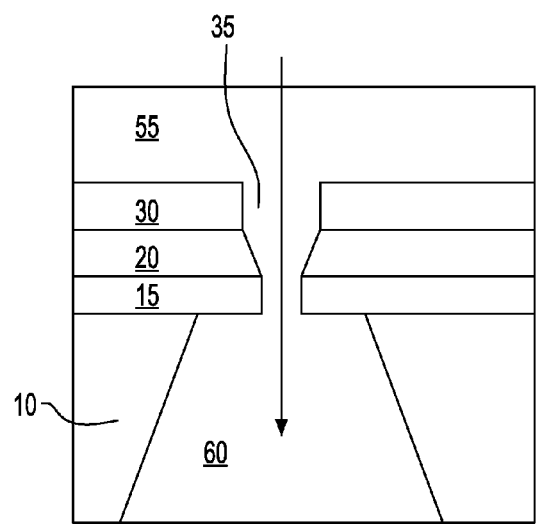
FIG. 7 depicts one embodiment of a fluidic channel 100E being utilized to provide a molecular solution, in accordance with another embodiment of the present disclosure.

The fluidic channels 100A, 100B, 100C, 100D of the present disclosure may be employed in DNA sequencing, molecular sensors, molecular filters and water treatment. FIG. 7 depicts one embodiment of a fluidic channel 100E being utilized to provide a molecular solution. Reference number 55 depicts a DNA solution in salt with a concentration gradient. The concentration is typically equal to approximately 500 nM. Reference number 60 depicts a salt solution. The salt solution is typically composed of 1M KCl/10 nM Tris.Cl. The PH of the solution is approximately 8.5. In one embodiment, DNA from the DNA solution in salt 55 translocate through the trapezoid shaped nanopore 35. In one example, the structure depicted in FIG. 7 leads to 1 translocation per second to 2 translocations per second. The arrow depicted in FIG. 7 illustrates the direction in which the translocations are traveling through the trapezoid shaped nanopore 35. A bias is applied to the structure depicted in FIG. 7 to control the translocation rate. The above noted applications for the fluidic channels 100A, 100B, 100C, 100D, 100E are provided for illustrative purposes, and are not intended to limit the application of the methods and structures disclosed in the present disclosure.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A fluidic structure comprising:
   a semiconductor on insulator substrate (SOI) having a single crystal semiconductor layer in direct contact with a topmost surface of a dielectric layer, wherein a bottommost surface of said dielectric layer is in direct contact with a topmost surface of a base semiconductor substrate;
   an array of nanopores having a trapezoid-shaped geometry, the array of nanopores extending through the single crystal semiconductor layer, wherein a first width at a first end of each nanopore of the array of nanopores is greater than the range of 15 to 20 nm, and a second width at a base of each nanopore of the array of nanopores is less than the range of 15 to 20 nm; and
   at least one fluidic channel located within said dielectric layer, but not said base semiconductor substrate, the at least one fluidic channel configured to connect at least two nanopores of the array of nanopores,
   wherein the fluidic structure includes at least one inlet provided by a nanopore of the array of nanopores and at least one outlet provided by another nanopore of the array of nanopores.

2. The fluidic structure of claim 1, wherein a standard deviation of the second width of the second end of each nanopore of the array of nanopores ranges from 1 to 5.

3. The fluidic structure of claim 1, wherein a standard deviation of the second width of the second end of each nanopore of the array of nanopores ranges from 1 to 3.

4. The fluidic structure of claim 1, wherein a concentration of the array of nanopores ranges from 1000 to $10^{12}$ pores/cm$^2$.

5. The fluidic structure of claim 1, wherein a concentration of the array of nanopores ranges from 1000 to $10^{10}$ pores/cm$^2$.

6. The fluidic structure of claim 1, wherein a concentration of the array of nanopores ranges from 10000 to $10^{16}$ pores/cm$^2$.

7. The fluidic structure of claim 1, wherein a concentration of the array of nanopores ranges from 1000 to $10^6$ pores/cm$^2$.

8. The fluidic structure of claim 1, wherein the first width ranges from 20 nm to 100 nm, and the second width ranges from 5 nm to 10 nm.

9. The fluidic structure of claim 1, wherein the first width ranges from 25 nm to 80 nm.

10. The fluidic channel of claim 1, wherein the second width ranges from 1 nm to 15 nm.

11. The fluidic channel of claim 1, wherein the second width ranges from 2 nm to 10 nm.

12. The fluidic structure of claim 1, wherein the single crystal semiconductor layer comprises Si, strained Si, SiC, SiGe, SiGeC, Si alloys, Ge, Ge alloys, GaAs, InAs, AlAs, InP, or a combination thereof.

13. The fluidic structure of claim 1, wherein the single crystal semiconductor material comprises a crystal plane selected from the group consisting of: <111>, <100> and a combination thereof.

14. The fluidic structure of claim 1, wherein the trapezoid shaped geometry is isosceles.

15. The fluidic structure of claim 14, wherein the trapezoid shaped geometry of each nanopore that is isosceles has a sidewall along a <111> direction.

16. A fluidic structure comprising:
   a semiconductor on insulator substrate (SOI) having a single crystal semiconductor layer in direct contact with a topmost surface of a dielectric layer, wherein a bottommost surface of said dielectric layer is in direct contact with a topmost surface of a base semiconductor substrate;
   etch mask portions located only on a topmost surface of the single crystal semiconductor portion of the semiconductor-on-insulator substrate;
   wherein an array of nanopores having a trapezoid-shaped geometry is located adjacent each of the etch mask portions and each of the single crystal semiconductor portions, wherein a first width at a first end of each nanopore of the array of nanopores located adjacent each etch mask portion is greater than the range of 15 to 20 nm, and a second width at a base of each nanopore of the array of nanopores and located adjacent each single crystal semiconductor portion is less than the range of 15 to 20 nm; and
   at least one fluidic channel located within said dielectric layer, but not said base semiconductor substrate, the at least one fluidic channel configured to connect at least two nanopores of the array of nanopores.

* * * * *